United States Patent
Coscia et al.

(10) Patent No.: US 12,280,234 B2
(45) Date of Patent: Apr. 22, 2025

(54) INTEGRATED ASEPTIC SYSTEM AND METHOD OF MAKING THE SAME

(71) Applicant: ENTEGRIS, INC., Billerica, MA (US)

(72) Inventors: Nicholas Coscia, Lexington, MA (US); Muhammad Siddiqui, Arlington, MA (US); Tate Vangsgard, Oakdale, MN (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 17/827,470

(22) Filed: May 27, 2022

(65) Prior Publication Data

US 2023/0122990 A1    Apr. 20, 2023

Related U.S. Application Data

(60) Provisional application No. 63/255,581, filed on Oct. 14, 2021.

(51) Int. Cl.
*A61M 39/18*    (2006.01)
*A61J 1/05*    (2006.01)

(52) U.S. Cl.
CPC ............... *A61M 39/18* (2013.01); *A61J 1/05* (2013.01)

(58) Field of Classification Search
CPC .. A61J 1/10; A61J 1/05; A61J 1/1475; A61M 39/18
See application file for complete search history.

(56) References Cited

U.S. PATENT DOCUMENTS

| | | | | |
|---|---|---|---|---|
| 3,519,158 | A | * | 7/1970 | Anderson ............ B65D 51/002 215/247 |
| 4,434,822 | A | * | 3/1984 | Bellamy ............... A61J 1/2089 604/7 |
| 6,068,031 | A | * | 5/2000 | Lataix .................... B65B 55/00 141/346 |
| 6,485,479 | B1 | * | 11/2002 | Knierbein ................ A61J 1/10 604/411 |
| 2009/0235619 | A1 | * | 9/2009 | Ostler ................... A61J 1/1406 53/469 |
| 2012/0111440 | A1 | * | 5/2012 | Schrader ................ A23L 3/001 141/85 |
| 2012/0284991 | A1 | * | 11/2012 | Kusz ..................... A61M 39/12 137/315.01 |
| 2015/0113919 | A1 | * | 4/2015 | Provitera ............... B29C 65/02 53/440 |
| 2016/0114922 | A1 | * | 4/2016 | Boira Bonhora ..... A61J 1/1481 383/42 |
| 2017/0203868 | A1 | * | 7/2017 | Py .......................... B65B 55/06 |
| 2019/0151199 | A1 | * | 5/2019 | Brosch ................... B32B 27/08 |

* cited by examiner

*Primary Examiner* — Ariana Zimbouski

(57) ABSTRACT

A bag assembly that includes a bag portion having first and second walls defining an interior and an opening. The interior is formed by the first and second walls of the bag portion being attached to each other along at least a portion of a perimeter of the bag assembly up to one end of the bag portion. Portions of the first and second walls of the bag portion that are not attached to each other form the opening. The bag assembly also includes an aseptic system for sterile connection and disconnection of the bag assembly from a sterile process, the aseptic system being continuously formed at an interface between the aseptic system and the one end of the bag portion. The aseptic system includes an internal passage to allow fluid communication with the interior of the bag portion and the sterile process.

15 Claims, 8 Drawing Sheets

INTEGRATED ASEPTIC SYSTEM AND METHOD OF MAKING THE SAME

FIELD

This disclosure relates generally to a bag assembly for containing a fluid. More specifically, the disclosure relates to a bag assembly that includes an aseptic system for providing an aseptic fluid path from the bag assembly to a processing device.

BACKGROUND

Chemical and/or biological processes can utilize or produce process materials that are stored within storage containers, such as bags, containing pharmaceutical or biological fluids. Tubing or other types of coupling and connectors may be utilized to supply the process material and/or reactants into the storage container. The process materials may need to be frozen or otherwise kept at low temperatures within the storage container. Tubing or other types of coupling may then be utilized to remove the process material from the storage container.

SUMMARY

In an embodiment, a bag assembly includes a bag portion having first and second walls defining an interior and an opening. The interior is formed by the first and second walls of the bag portion being attached to each other along at least a portion of a perimeter of the bag assembly up to one end of the bag portion. Portions of the first and second walls of the bag portion that are not attached to each other form the opening. The bag assembly also includes an aseptic system for sterile connection and disconnection of the bag assembly from a sterile process, the aseptic system being continuously formed at an interface between the aseptic system and the one end of the bag portion. The aseptic system includes an internal passage to allow fluid communication with the interior of the bag portion and the sterile process.

In an embodiment, a fitment is further included, where the fitment includes first and second outer surfaces extending between opposing end points and a fitting extending transversely from the fitment. The continuous formation at the interface is formed by the fitting of the fitment being integrally molded with the aseptic system as a single molded piece, where the internal passage is formed transversely through the aseptic system, the fitting, and the fitment for the fluid communication with the interior of the bag portion.

In an embodiment, a fitment is further included, where the fitment includes first and second outer surfaces extending between opposing end points and a fitting extending transversely from the fitment. The continuous formation at the interface is formed by the fitting of the fitment and the aseptic system being over molded with a melt-processable material to connect the aseptic system and the fitting of the fitment in a way such that the internal passage of the aseptic system is connected to an internal passage through the fitting and the fitment to the interior of the bag portion.

In an embodiment, the aseptic system is continuously formed with the interface and the first and second walls of the bag portion in a way such that the internal passage is formed through the aseptic system to connect directly to the interior of the bag portion. In an embodiment, the interface includes a connection piece extending transversely from the aseptic system, wherein outer surfaces of the connection piece are continuously formed with the first and second walls of the bag portion.

In an embodiment, a method for manufacturing a bag assembly includes forming a bag portion of the bag assembly by attaching together first and second walls along at least a portion of a perimeter of the bag assembly up to at least one end of the bag portion to define an interior and an opening of the bag portion, where portions of the first and second walls of the bag portion that are not attached to each other form the opening. The aseptic system is then continuously formed with the one end of the bag portion by having a continuously formed interface between the aseptic system and the bag portion, the aseptic system for providing sterile connection and disconnection of the bag assembly from a sterile process, where the aseptic system includes an internal passage to allow fluid communication with the interior of the bag portion and the sterile process.

BRIEF DESCRIPTION OF THE DRAWINGS

References are made to the accompanying drawings that form a part of this disclosure, and which illustrate embodiments in which the systems and methods described in this specification can be practiced.

Like reference numbers represent like parts throughout.

DETAILED DESCRIPTION

Figure 1:
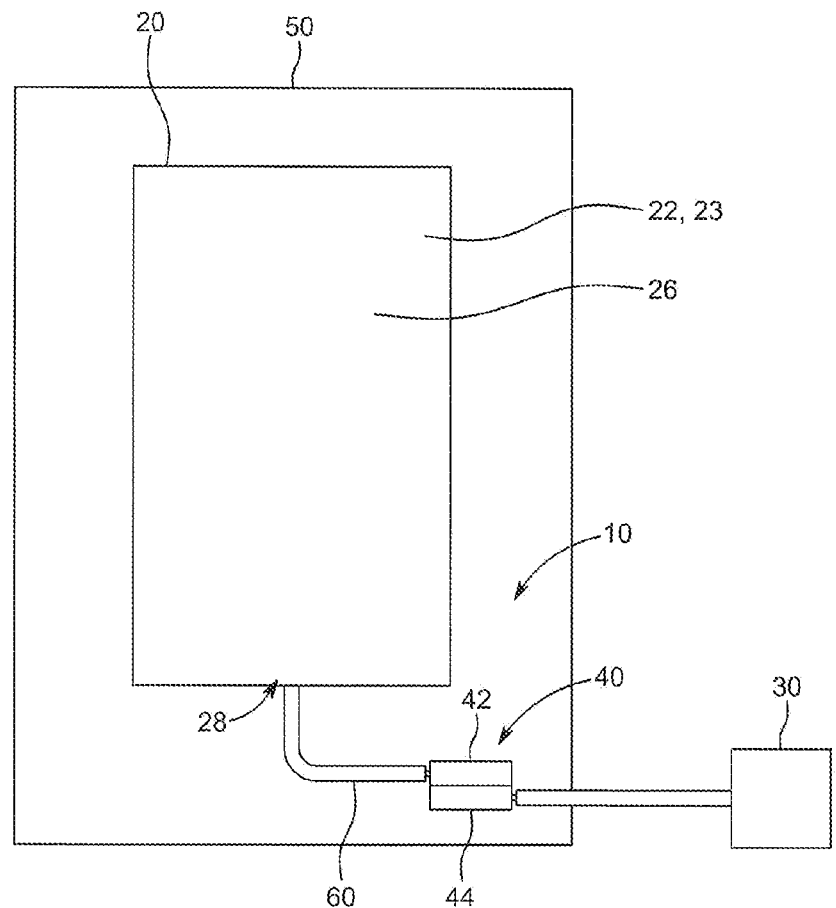
FIG. 1 is a schematic diagram of an embodiment of a low-temperature storage container aseptically connected to a processing device with a continuously formed aseptic system.

This disclosure relates generally to a bag assembly for containing a fluid. More specifically, the disclosure relates to a bag assembly that includes an aseptic system for providing an aseptic fluid path from the bag assembly to processing equipment. The term aseptic as used herein is at least related to creating a barrier or fluid path that remains unbroken to keep the internal fluid of the bag assembly substantially free of contaminants from an external environment to maintain the sterility of the internal components.

Some chemical and/or biological processes utilize or produce process materials that are stored within storage containers, such as bags, containing pharmaceutical or biological fluids. Tubing or other types of coupling and connectors may be utilized to supply the pharmaceutical or biological fluids into the storage container. The pharmaceutical or biological fluids may need to be frozen or otherwise kept at low temperatures within the storage container. Tubing or other types of coupling may then be utilized to remove the pharmaceutical or biological fluids from the storage container. A fluid includes, but is not limited to, a substance that flows or deforms when a shear stress is applied. A fluid can include, for example, a liquid.

In some cases, the pharmaceutical or biological fluids in the storage container needs to be processed aseptically during the supply, storage, testing, and/or removal of the pharmaceutical or biological fluids. That is, the pharmaceutical or biological fluids are provided in a sterilized environment and are transferrable from the storage container under sterile conditions. For example, films, caps, valves, or similar sealing devices that maintain a hermetic seal can be attached and/or coupled to the storage container and/or any processing equipment for the aseptic connection/disconnection of the storage container to any processing equipment. The film, caps, valves, or similar sealing devices can then be punctured, removed, and/or turned to allow the transfer of the sterile pharmaceutical or biological fluids to the processing equipment when the storage container is coupled to the processing equipment and disconnected using films, caps, automatic shut-off valves, or similar devices that allow an aseptic disconnect functionality.

Such aseptic systems are known in the art. For example, Colder Products Company sells sterile connectors such as the AseptiQuik® Sterile Connectors, the Steam-Thru® Connection, and SaniQuik®.

It was observed, however, that when such storage container is coupled to the aseptic system via tubing, which can use a hose barb and tri-clamp connection system for connecting the same, and stored at cryogenic temperatures of −190° C. or lower, the ultra-cold temperature caused a leakage in the storage container that allowed ingress of the cryogenic fluid, e.g., liquid nitrogen or similar, into the storage container. Thus, causing failure of the storage container. Without wishing to be bound by theory, it is understood that upon immersion of the storage container in the cryogenic fluid, the storage container, tubing, and/or aseptic system, which can be made of different materials having different thicknesses and having different coefficients of thermal expansion (and contraction), contract at different rates and/or have different thermal properties, e.g., rigidity/flexibility, especially at the ultra-cold cryogenic temperatures. Thus, when the storage container, tubing, and the aseptic system are immersed into the cryogenic fluid, due to the different contraction rates and/or different thermal properties, the coupling between the storage container and the aseptic system fails, which allows ingress of the nitrogen, either in liquid or gas form, into the storage container.

FIG. 1 is a schematic diagram of a bag assembly 10 that overcomes the deficiencies of the prior art. The bag assembly 10 includes a bag portion 20 that is aseptically connected to a processing device 30 using a low-temperature aseptic system 40 that is continuously formed at an interface between the aseptic system 40 and the bag portion 20. The bag assembly 10 can be stored in a bag holder 50 in a cryogenic system. The sterile process can include the processing device 30 which can include equipment that supplies the process material, e.g., the pharmaceutical or biological fluids, from a sterile process or sterile reactants that form the process material to fill the bag portion 20 and/or equipment that uses the process material in the bag portion 20 for sterile processing.

Bag portion 20 can be a low-temperature fluid storage container. For example, the bag portion 20 includes first and second walls 22, 23 that define an interior 26 and an opening 28. The interior 26 is formed by the first and second walls 22, 23 being attached to each other along at least a portion of a perimeter of the bag portion 20 up to one end of the bag portion 20, where the opening 28 is formed by portions of the first and second walls 22, 23 of the bag portion 20 that are not attached to each other. In some embodiments, the first and second walls 22, 23 are welded or bonded together along their respective edges along a majority of the perimeter of the bag portion 20 up to the one end of the bag portion that has the opening 28. Exemplary welding or bonding techniques can include, but are not limited to heat bonding, impulse welding, laser welding, ultrasonic welding, platen welding, or similar fusion bonding/melt welding techniques. It is appreciated that the first and second walls 22, 23 of the bag portion 20 are attached to each other without the use of adhesives, solvents or binders, since eliminating the use of adhesives, solvents or binders in the construction of the bag assembly can enhance the overall purity of the final assembly as the number of sources of potential leachable and extractable materials are reduced, which helps to maintain the purity of the fluid in the bag assembly.

Each of the first and second walls 22, 23 of the bag portion 20 can be formed from at least one sheet of a polymeric film and more particularly, from at least one sheet of a fluoropolymer film. In some embodiments, the fluoropolymer film includes an ethylenetetrafluoroethylene (ETFE) polymer, a polychlorotrifluoroethylene (PCTFE) polymer, a polyvinyl fluoride (PVF) polymer, a polyvinylidene fluoride (PVDF) polymer or a combination thereof. In another embodiment, the fluoropolymer film includes an ethylenetetrafluoroethylene (ETFE) polymer, a polyvinyl fluoride (PVF) polymer, a polyvinylidene fluoride (PVDF) polymer or a combination thereof. In still another embodiment, ETFE may be particularly suited for construction of the bag assemblies. In some embodiments, the first and second walls 22, 23 of the bag portion 20 are formed from a single sheet of a fluoropolymer film. The single sheet of fluoropolymer film excludes any intervening layers such as barrier layers, adhesive layers tie layers or combinations thereof. Use of a single sheet of a fluoropolymer film having no intervening layers reduces the potential number of sources of leachables or extractables, and may enhance the overall purity of the final assembly and fluid therein.

Each sheet of the fluoropolymer film that form the first and second walls 22, 23 of the bag portion 20 can have a thickness of about 2.5 mil (63.5 μm) to about 20 mil (508 μm), or of about 5 mil (127 μm) to about 15 mil (381 μm). In one embodiment, each sheet of fluoropolymer film forming the walls 22, 23 has a thickness of about 8 mil (203.2 μm).

The bag portion 20 is aseptically connected to the low-temperature aseptic system 40 by being continuously formed at an interface between the aseptic system 40 and the bag portion 20. The aseptic system 40 allows the sterile connection and disconnection of the bag assembly from the sterile process. The aseptic system 40 includes a first connector/disconnector 42 and a second connector/disconnector 44, where the first connector/disconnector 42 is fluidly connected to the bag portion 20 and the second connector/disconnector 44 is fluidly connected to the processing device 30. The coupling of the first connector/disconnector 42 and the second connector/disconnector 44 connects fluid passages in the first connector/disconnector 42 and the second connector/disconnector 44 to form a sealed fluid connection that extends transversely through the coupled connectors 42, 44.

The first connector/disconnector 42 and the second connector/disconnector 44 can be coupled together by any suitable structure for forming a mechanical connector to form a snap-fit, pressure-fit, or the like. For example, a retaining feature(s) of the first connector/disconnector 42 can be any suitable structure for forming a mechanical connector with a respective complementary retaining feature (s) of the second connector/disconnector 44. The retaining features can include, for example, slots, tabs, flanges, detents, hooks, or any other suitable structures for mechanical engagement with other complementary structures.

The low-temperature aseptic system 40 can include a pair of removable films (not shown) that can seal the transversely formed fluid passages from the ambient environment prior to the coupling of the connectors 42, 44. The removable films respectively cover and seal the openings of the respective first and second fluid passages of the connectors 42, 44. The removable films are configured to maintain the fluid passages as aseptic prior to the coupling of the connectors 42, 44. For example, each film prevents contaminants from the environment (e.g., as dust, moisture, etc.) from entering the respective fluid passage that is used to fluidly connect the transversely formed fluid passages in the coupled connectors 42, 44. The removable films are removed once the connectors 42, 44 have been connected. For example, the removable films are removed after being compressed between the connected connectors 42, 44.

The polymer material(s) of the connectors 42, 44 is generally a polymer that is generally non-reactive (e.g., non-reactive with air, non-reactive with the process material or the reactants used in the bag assembly) and a material that is compatible with the bag portion. For example, each of the connectors 42, 44 in an embodiment comprises a fluoropolymer that is able to be fused or bonded, e.g., melt or fusion bonded, with the bag portion.

At least the first connector/disconnector 42 of the aseptic system 40 is continuously formed at the interface between the aseptic system 40 and one end of the bag portion 20 so that an uninterrupted flow path is formed between the aseptic system 40 and the bag portion 20. The continuous formation of the aseptic system 40 and the bag portion 20 prevents any ingress of contaminants from the environment outside of the bag assembly, especially during the cryogenic freezing of the bag assembly since no leakage points exist between the aseptic system 40 and the bag portion 20. For example, the continuous formation can be a continuous formation of polymer formed by integrally molding the first connector/disconnector 42 at the interface of the bag portion 20, over-molding a connection between the first connector/disconnector 42 and the bag portion 20 at the interface, or continuously forming the first connector/disconnector 42 directly with the bag portion 20 at the interface. That is, it is appreciated that the continuous formation of the aseptic system and the bag portion results in a bag assembly that is formed as a single piece, e.g., does not include any intermediary non-continuously formed connections or use any clamps between the aseptic system and the bag portion by using bonding, fusing, or molding processes so that the bag assembly is formed as a single piece. Thus, no leakage points exist between the bag assembly and the aseptic system, even during cryogenic freezing.

In one embodiment of the invention, as seen schematically in FIG. 1, the first connector/disconnector 42 is continuously formed at the interface, which includes tubing 60, with the bag portion 20. Specifically, a first end of the tubing 60 is continuously formed with the aseptic system 40 so that an opening of an internal passage in the aseptic system 40, e.g., the internal passage in the first connector/disconnector 42, is connected to the tubing 60. The other end of tubing 60 is continuously formed with the bag portion 20. In so doing, the interior of the bag portion 20 is in fluid communication with the aseptic system 40 through such interface.

Figure 2A:
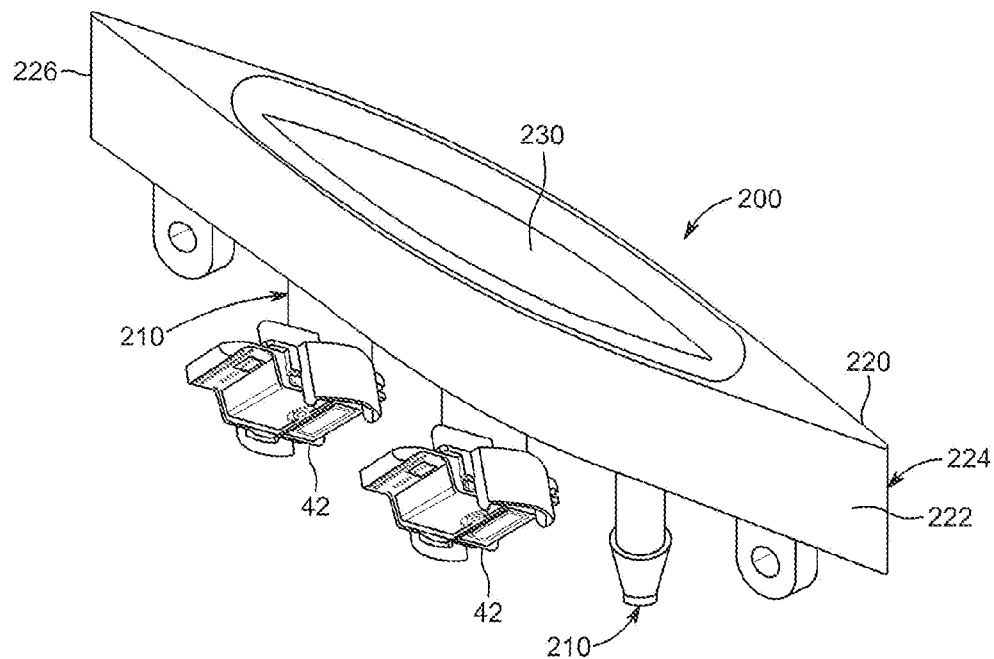
FIG. 2A is an enlarged front perspective view of a continuously formed fitment and aseptic system according to an embodiment.

FIGS. 2A-2D illustrates one embodiment of the invention, where the interface, which includes tubing 60, is integrally molded with at least one fitment 200 and at least one aseptic system 40. As seen in FIG. 2A, the fitment 200 includes first and second outer surfaces 220, 222 that extend between opposing end points 224, 226 to form a structure that is able to be attached, e.g., by secondary bonding techniques, to the opening 28 of the bag portion 20. The fitment 200 also includes at least one fitting 210, which is a part of the tubing 60, that extends transversely from the fitment 200, a fitment opening 230 that allows communication between the interior of the bag portion 20 and the at least one fitting 210, and at least the first connector/disconnector 42 of the aseptic system 40 continuously formed with the at least one fitting 210.

In this embodiment, the tubing 60 (formed at least in part by the fitting 210), the fitment 200, and the at least one aseptic system 40 are integrally molded as a single piece, e.g., using a single mold during the molding process or using injection molding, cast molding (e.g., two-part cast molding or the like), thermoforming. Accordingly, the interface is formed directly with or continuously formed of polymer with the fitment 200 and the first connector/disconnector 42 of the at least one aseptic system 40.

Figure 2B:
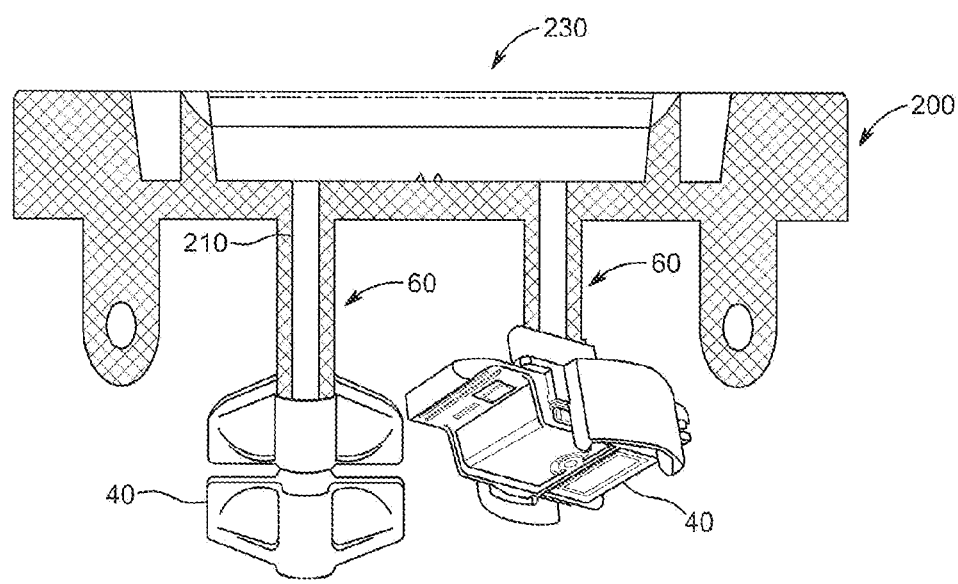
FIG. 2B is an enlarged cross-sectional view of a continuously formed fitment and aseptic system according to an embodiment.

As seen in FIG. 2B, in an embodiment of the invention having two different aseptic systems, such structure has an uninterrupted flow path between the interior of the bag portion and the processing fluid with at least the first connector/disconnector 42 of the aseptic system 40 through the fitment opening 230, a fluid channel through the tubing/fitting 210, and the internal fluid passage of the first connector/disconnector 42 that is formed transversely through the aseptic system 40. Thus, the integrally molded fitment and aseptic system are continuously formed as a single piece having a continuously formed internal passage so that the interior of the bag portion is in fluid communication with the aseptic system. Accordingly, no additional tubing or connectors are required to couple the aseptic system to the bag portion, which eliminates leakage points between the bag portion 20, the fitment 200, and the aseptic system 40, as further discussed below. It is appreciated that while the fitment 200 and first connector/disconnector 42 are discussed above as being separate pieces, the fitment and first connector/disconnector are not separate elements, but are provided as a single piece that is secondarily bonded to the bag portion. It is also further appreciated that gaskets can be provided between the connection of the fitment 200, the tubing/fitting 210, and first connector/disconnector 42, as necessary. The gasket(s) can be press-fitted into the connection or molded to the fitment, tubing/fitting, and/or the first connector/disconnector.

Figure 2C:
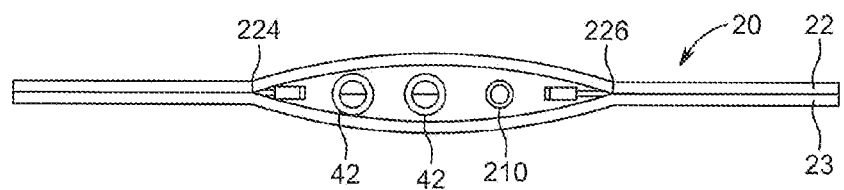
FIG. 2C is a bottom view of the continuously formed fitment and aseptic system according to FIG. 2A attached to a bag portion.
Figure 2D:
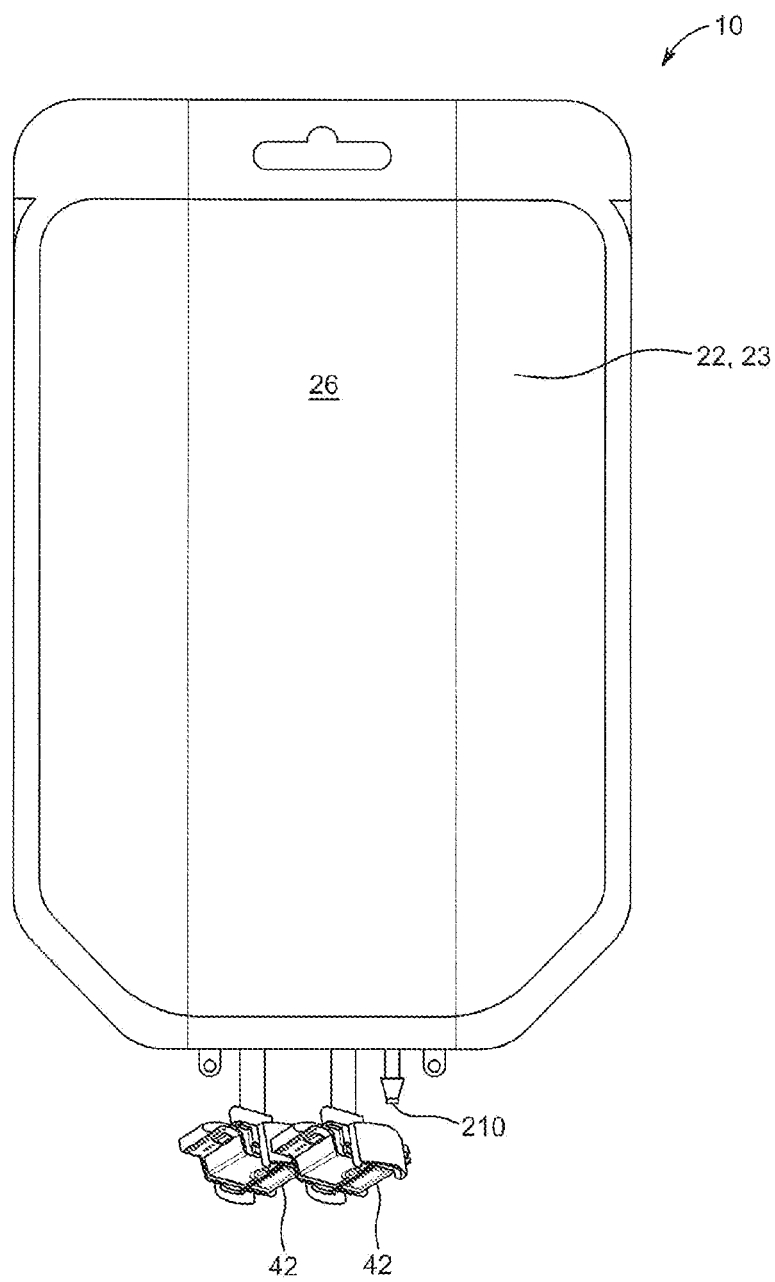
FIG. 2D is a front view of the continuously formed fitment and aseptic system according to FIG. 2A attached to the bag portion.

FIGS. 2C and 2D illustrate the fitment 200 and first connector/disconnector 42 combination attached to the opening 28 of the bag portion 20 between the first and second walls 22, 23. Specifically, the first and second outer surfaces 220, 222 of the fitment 200 and first connector/disconnector 42 combination that extend between opposing end points 224, 226 are attached to the first and second walls 22, 23 of the bag portion 20 through the opening 28 of the bag portion 20, thus placing the fitment 200 and first connector/disconnector 42 combination in fluid communication with the interior 26 of the bag portion 20. The first and second walls 22, 23 of the bag portion 20 are welded or bonded to the first and second outer surfaces 220, 222 of the fitment 200 and first connector/disconnector 42 combination such that a continuous bond or weld is formed about the entire perimeter of the bag assembly 10. The attachment of the first and second walls 22, 23 along a continuous surface removes any points of weakness that would occur if, for example, the walls were bonded to a fitment having sharper angled edges or to a fitment with a more circular shape, and may result in a more robust attachment between the bag portion 20 and the fitment 200 and first connector/disconnector 42 combination. Any suitable bonding or welding technique for compatible materials can be used to attach the first and second walls 22, 23 of the bag portion 20 to the first and second outer surfaces 220, 222 of the fitment 200 and first connector/disconnector 42 combination. For example, the first and second walls 22, 23 of the bag portion 20 may be attached to the outer surfaces 220, 222 of the fitment 200 and first connector/disconnector 42 combination using heat bonding, laser welding, ultrasonic welding, heat sealing, or platen welding techniques. In many embodiments, the attachment between the first and second walls 22, 23 of the bag portion 20 and the first and second outer surfaces 220, 222 of the fitment 200 and first connector/disconnector 42 combination is made without the use of adhesives, solvents or binders, which can reduce the potential for leachables and extractables in the final bag assembly 10. Thus, the integrally molded fitment and aseptic system combination and the bag portion are continuously formed as a single piece, so that no leakage points exist between the bag portion 20 and the aseptic system 40.

In an embodiment, the entire fitment 200 is made of a fluoropolymer which may be a homopolymer or a copolymer of a fluoropolymer, for example PFA. Accordingly, the fitment 200 and first connector/disconnector 42 combination and the first and second walls 22, 23, of the bag portion 20 can be made of one or more of the same polymers to have suitable joining characteristics relative to each other, e.g., similar melting temperatures and flow characteristics to allow thermal/fusion bonding or fusing, chemical resistance or compatibility, and/or other properties required by an application for a fluid containment system, such as UV blocking and the like.

Figure 3:
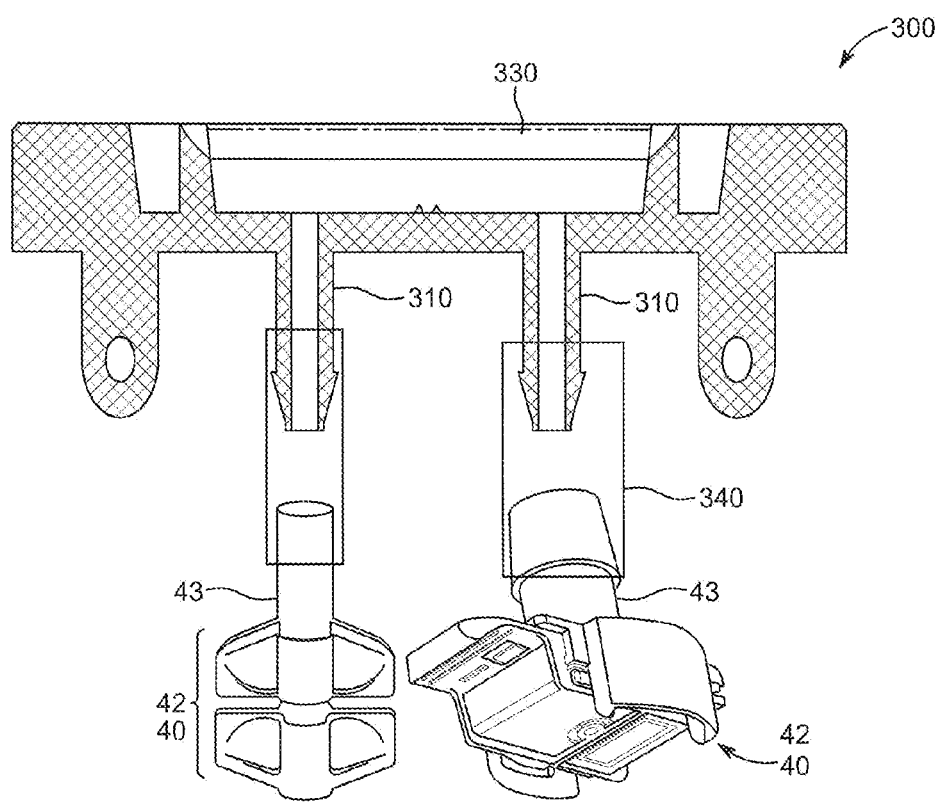
FIG. 3 is an enlarged cross-sectional view of the continuously formed fitment and aseptic system according to another embodiment.

FIG. 3 is a perspective view of another embodiment of the bag assembly having the aseptic system continuously formed at the interface with the bag portion. In this embodiment, the at least one fitment 300 includes at least one fitting 310 that extends transversely from the fitment 300 and a fitment opening 330. The aseptic system 40 is provided separately, where the first connector/disconnector 42 includes connection piece 43 that extends transversely from the first connector/disconnector 42. The connection piece 43 includes an internal passage that is in fluid communication with the internal passage of the first connector/disconnector 42 and the aseptic system 40.

In this embodiment, the interface includes the tubing 60 which is formed by over-molding a melt-processable material 340 over the connection piece 43 of the first connector/disconnector 42 and the fitting 310 of the fitment 300, where the melt-processable material 340 can be a polymer that has suitable joining characteristics with the fitment 310 and the first connector/disconnector 42, e.g., a fluoropolymer or polymer having similar melting temperatures and flow characteristics to allow thermal/fusion bonding or fusing, chemical resistance or compatibility, and/or other properties required by an application for a fluid containment system, such as UV blocking and the like. In many embodiments, the attachment between the melt-processable material 340 and the fitment 300 and the first connector/disconnector 42 is made without the use of adhesives, solvents or binders, which can reduce the potential for leachables and extractables in the final bag assembly 10.

As seen in FIG. 3, by over-molding the melt-processable material 340 over the connection piece 43 and the fitting 310, the fitment 300 is formed directly with or continuously formed of polymer with the first connector/disconnector 42 of the at least one aseptic system 40. Such structure has an uninterrupted flow path between the interior of the bag portion 20 and the processing fluid with at least the first connector/disconnector 42 of the aseptic system 40, the fitment opening 330, a fluid channel through the fitting 310, and the internal fluid passage of the first connector/disconnector 42. Thus, the over-molded fitment and aseptic system are continuously formed so that the interior of the bag portion is in fluid communication with the aseptic system. Accordingly, no additional tubing or connectors are required to couple the aseptic system to the bag portion, which eliminates leakage points between the bag portion 20, the fitment 200, and the aseptic system 40. It is appreciated that while FIG. 3 schematically shows the overmolding of the connection piece 43 and the fitting 310 as being separate, the connection piece 43 can be fitted over the barb-type connection of the fitting 310.

Similar to the above embodiment, the fitment 300 and aseptic system 40 combination can then be attached to the opening of the bag portion between the first and second walls of the bag portion (not shown) so that the fitment 300 and aseptic system 40 combination is in fluid communication with the interior of the bag portion. The first and second walls of the bag portion can be welded or bonded to the first and second outer surfaces of the fitment 300 and aseptic system 40 combination such that a continuous bond or weld is formed about the entire perimeter of the bag assembly 10, where any suitable bonding or welding technique can be used to attach the first and second walls of the bag portion to the first and second outer surfaces of the fitment 300 and aseptic system 40 combination, as discussed above. Thus, the over-molded fitment and aseptic system are continuously formed, so that no leakage points exist between the bag portion 20 and the aseptic system 40.

Figure 4A:
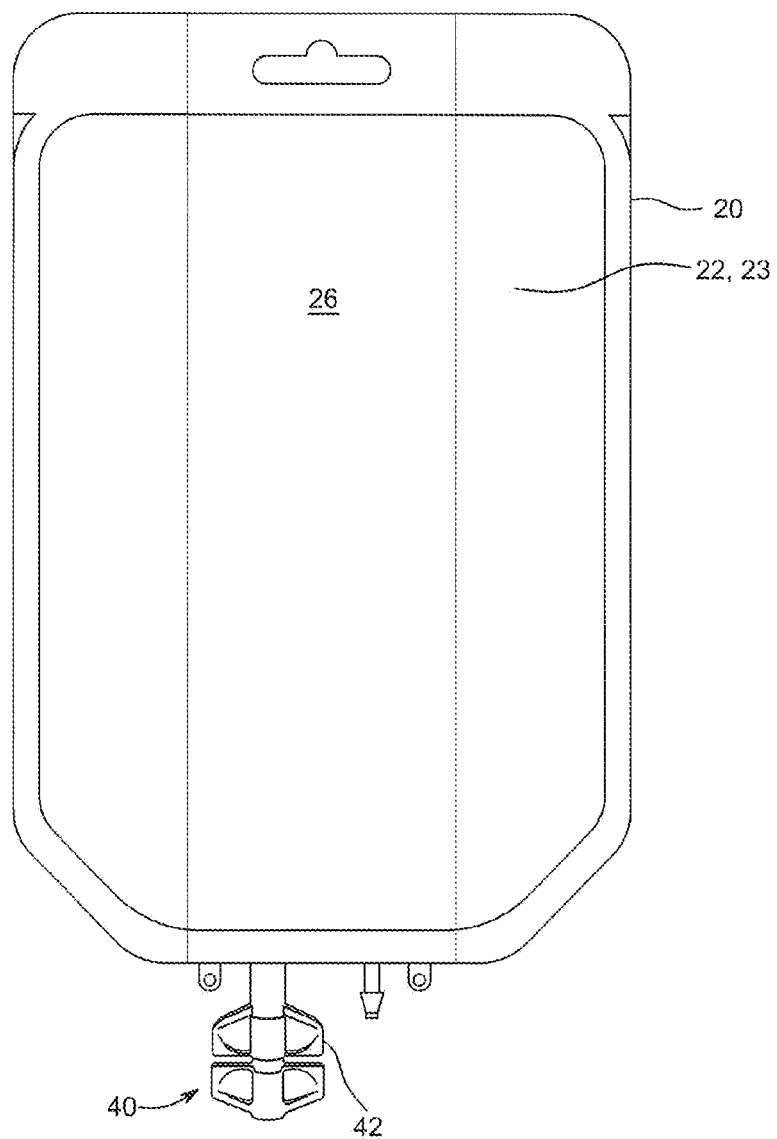
FIGS. 4A and 4B are front views of the continuously formed fitment and aseptic system according to yet another embodiment.
Figure 4B:
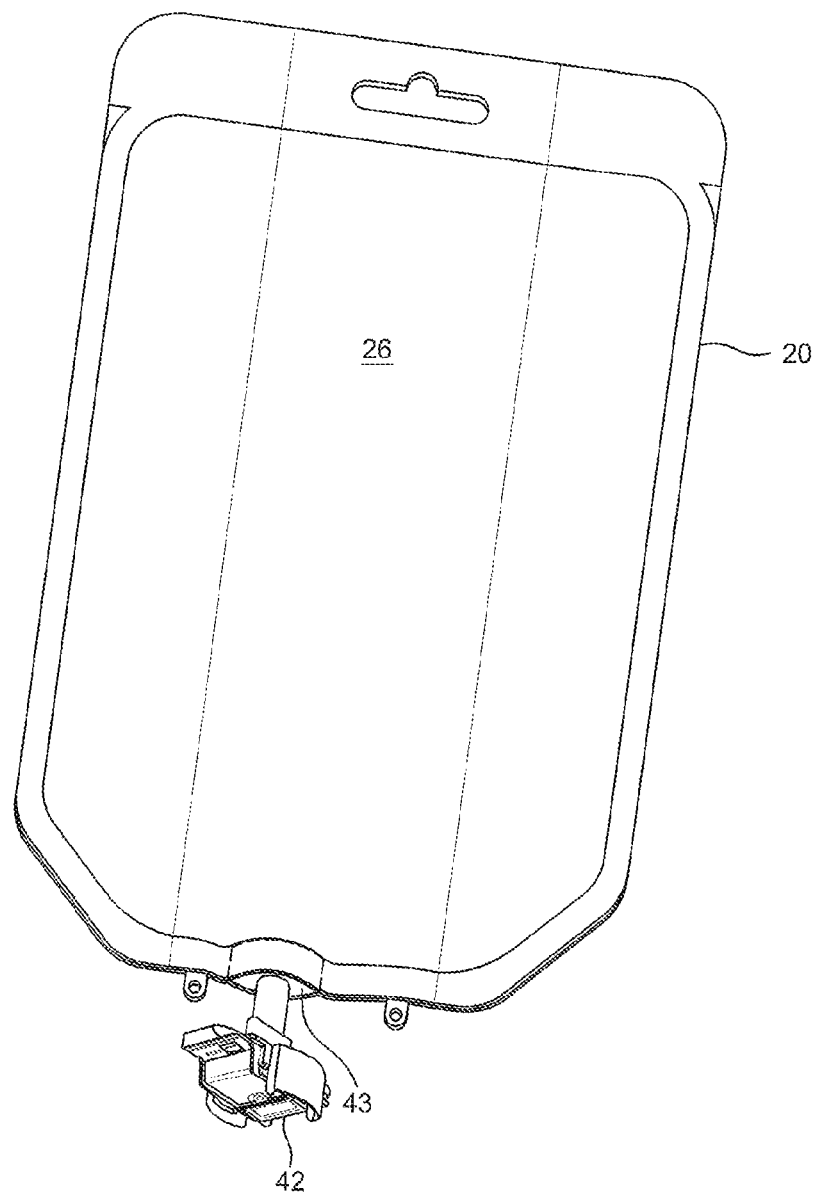

FIGS. 4A and 4B show another embodiment in which the fitment, as described above, is not used in the continuous formation between the aseptic system and the bag portion. Rather, the first connector/disconnector 42 of the aseptic system 40 is directly connected to the bag portion 20 at the interface, where an internal passage of the first connector/disconnector 42 is connected directly with the interior 26 of the bag portion 20.

FIG. 4A illustrates the first connector/disconnector 42 being continuously formed with the bag portion 20 at the interface by being connected between the first and second walls 22, 23 of the bag portion 20 so that the first connector/disconnector 42 is in fluid communication with the interior 26 of the bag portion 20. The first and second walls 22, 23 of the bag portion 20 can be welded or bonded to outer surfaces of the first connector/disconnector 42 such that a continuous bond or weld is formed about the entire perimeter, where any suitable bonding or welding technique discussed above for bonding or welding the fitment to the bag portion can also be used to attach the first and second walls 22, 23 of the bag portion 20 to the outer surfaces of the first connector/disconnector 42.

By directly connecting the first connector/disconnector 42 at the interface at the bag portion 20, the first connector/disconnector 42 is formed directly with or continuously with or continuously formed of polymer with the bag portion 20. Such structure allows the fluid communication between the interior of the bag portion 20 and the processing fluid with at least the first connector/disconnector 42 of the aseptic system 40 by being fluidly connected through the internal fluid passage of the first connector/disconnector 42 that is formed transversely through the aseptic system. Thus, the aseptic system is continuously formed with the bag portion, so that no leakage points exist between the bag portion 20 and the aseptic system 40.

FIG. 4B shows another embodiment in which the first connector/disconnector 42 is continuously formed with the bag portion 20 at the interface by having a connection piece 400 of the first connector/disconnector 42 connected between the first and second walls 22, 23 of the bag portion 20 so that the first connector/disconnector 42 is in fluid communication with the interior 26 of the bag portion 20. The first and second walls 22, 23 of the bag portion 20 can be welded or bonded to outer surfaces of the connection piece 400 of the first connector/disconnector 42 such that a continuous bond or weld is formed about the entire perimeter, where any suitable bonding or welding technique discussed above for bonding or welding the fitment to the bag portion can also be used to attach the first and second walls 22, 23 of the bag portion 20 to the outer surfaces of the connection piece 400 of the first connector/disconnector 42. It is appreciated that the connection piece can be a straight tube and/or have a geometric shape, for example, an ovular shape, to facilitate the bonding or welding of the outer surfaces of the connection piece 400 with the first and second walls 22, 23 of the bag portion 20.

By directly connecting the connection piece 400 of the first connector/disconnector 42 with the bag portion 20, the first connector/disconnector 42 is formed directly with or continuously with the bag portion. Such structure has an uninterrupted flow path between the interior of the bag portion 20 and the processing fluid with at least the first connector/disconnector 42 of the aseptic system 40 by being fluidly connected through the internal fluid passage of the first connector/disconnector 42 that is formed transversely through the aseptic system 40. Thus, the aseptic system 40 is continuously formed with the bag portion 20, so that no leakage points exist between the bag portion 2 and the aseptic system 40.

Accordingly, any of the above identified filled bag assemblies 10 are configured to be stored at frozen temperatures (e.g., temperatures of less than 0° C.). In an embodiment, the bag assembly 10 is configured to be stored at cryogenic temperatures of −150° C. or lower. In an embodiment, the bag assembly 10 is configured to be stored at cryogenic temperatures of −190° C. or lower. In an embodiment, the bag assembly 10 can also be heated back to ambient temperature without having any substantial deformation. Substantial deformation includes, for example, visible cracking in the material, a shrinkage or expansion relative to its original shape at ambient temperature that can interfere with the connection(s) or adversely affect sealing of said connection(s). Temperature retraction testing can be performed according to ASTM D1329, ISO 2921, or any other suitable testing methodology for determining suitable retraction properties of the material at temperatures that may be used. Brittleness testing can be performed according to ASTM D2137, ISO 28702, or any other suitable testing methodology for determining resistance to cracking at temperatures that may be used.

Not wishing to be bound by theory, it was surprisingly found that by having the continuous formation or having the continuous formation of polymer of the aseptic system with the fitment/bag portion, potential leak points are eliminated since no connectors or clamps are provided between the bag portion and the aseptic system. In so doing, at least because the aseptic system, the bag portion, and/or the fitment are formed from the same or similar polymers, e.g., a fluoropolymer, having the same or similar coefficients of thermal contraction and/or thermal properties, during the cryogenic freezing process, the aseptic system, the bag portion, and/or the fitment contract at the same rate and/or have the same or similar thermal properties, which eliminates any leak points to have an uninterrupted flow path from the bag portion to the aseptic system, so that the bag assembly is able to maintain structural integrity and prevent the ingress of the cryogenic fluid, e.g., nitrogen, into the bag assembly.

Figure 5:
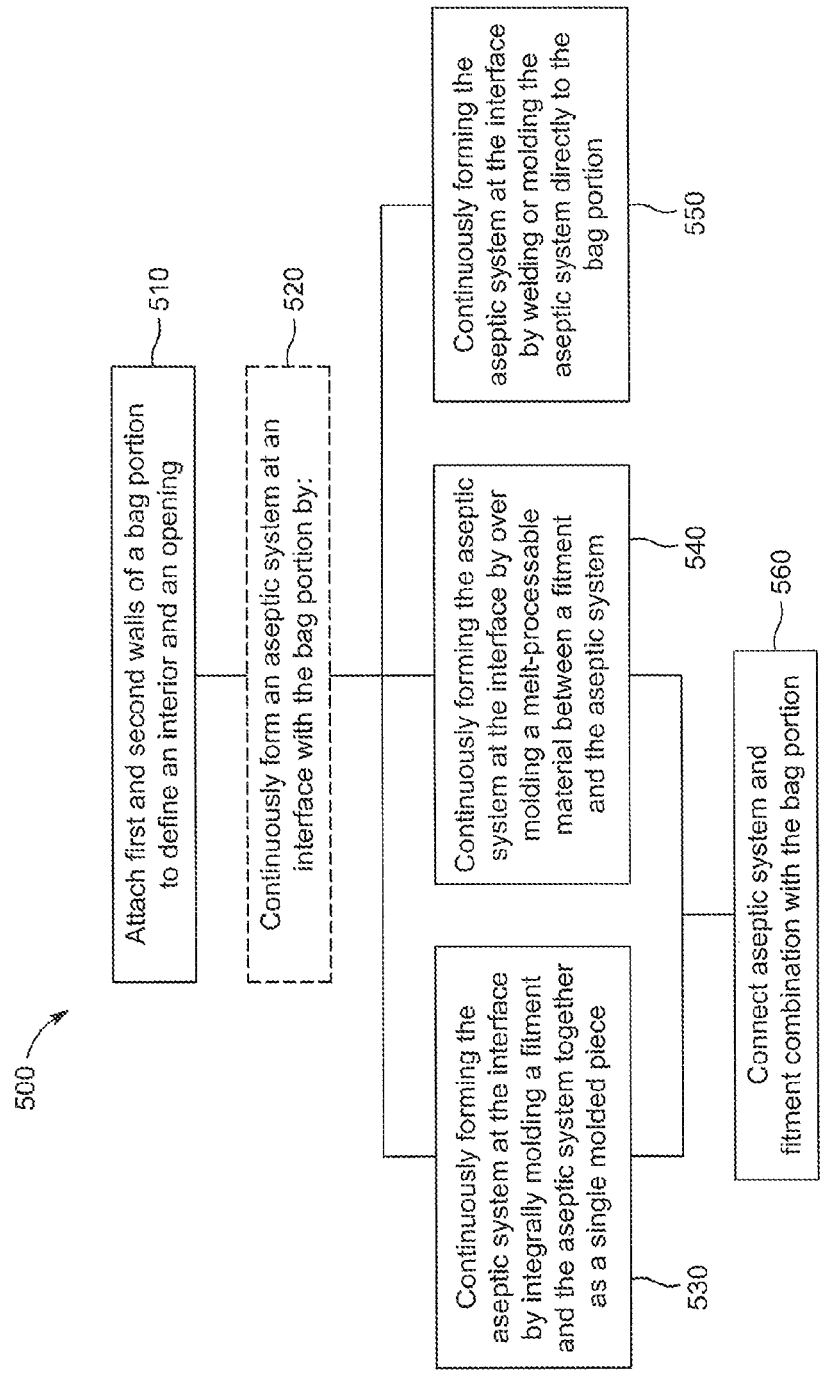
FIG. 5 is a flowchart of a method of manufacturing a bag assembly, according to an embodiment.

FIG. 5 is a flowchart of a method of manufacturing a bag assembly, according to an embodiment. At 510, the bag portion is formed by attaching first and second walls of the bag portion to define an interior and an opening. The interior is formed by the first and second walls being attached to each other along at least a portion of a perimeter of the bag portion up to one end of the bag portion, where the opening is formed by portions of the first and second walls of the bag portion that are not attached to each other. Exemplary welding or bonding techniques can include, but are not limited to heat bonding, impulse welding, laser welding, ultrasonic welding, platen welding, or similar fusion bonding/melt welding techniques. It is appreciated that the first and second walls of the bag portion are attached to each other without the use of adhesives, solvents or binders, since eliminating the use of adhesives, solvents or binders in the construction of the bag assembly can enhance the overall purity of the final assembly as the number of sources of potential leachable and extractable materials are reduced, which helps to maintain the purity of the fluid in the bag assembly.

At 520, an aseptic system is then continuously formed at an interface with the bag portion. The continuous formation of the aseptic system with the bag portion can occur by:

A. Continuously forming the aseptic system at the interface by integrally molding a fitment and the aseptic system together as a single molded piece (at 530). In an embodiment, the fitment and aseptic system are integrally molded by using a single mold during the molding process, or using injection molding, cast molding using two-part cast molding, or thermoforming to form the aseptic system and fitment together as a single piece. Thus, the aseptic system is in fluid communication with the bag portion via an uninterrupted flow path through the fitment and aseptic system combination.

At 560, the aseptic system and fitment combination is then connected with the bag portion. For example, the first and second walls of the bag portion can be welded or bonded to the first and second outer surfaces of the fitment and aseptic system combination such that a continuous bond or weld is formed about the entire perimeter of the bag assembly. Any suitable bonding or welding technique can be used to attach the first and second walls of the bag portion to the first and second outer surfaces of the fitment and aseptic system combination. For example, the first and second walls of the bag portion may be attached to the outer surfaces of the fitment and aseptic system combination using heat bonding, laser welding, ultrasonic welding, heat sealing, or platen welding techniques. In many embodiments, the attachment between the first and second walls of the bag portion and the first and second outer surfaces of the fitment and aseptic system combination is made without the use of adhesives, solvents or binders, which can reduce the potential for leachables and extractables in the final bag assembly. Thus, the integrally molded fitment and aseptic system are continuously formed as a single piece, so that no leakage points exist between the bag portion and the aseptic system.

B. Continuously forming the aseptic system at the interface by over molding a melt-processable material between a fitment and the aseptic system (at 540). For example, in an embodiment, a tubing is formed by over-molding a melt-processable material over a connection piece of the first connector/disconnector of the aseptic system that extends transversely from the first connector/disconnector and a fitting of the fitment that extends transversely from the fitment, where the melt-processable material can be a polymer that has suitable joining characteristics with the fitment and the first connector/disconnector, e.g., a fluoropolymer or polymer having similar melting temperatures and flow characteristics to allow thermal/fusion bonding or fusing, chemical resistance or compatibility, and/or other properties required by an application for a fluid containment system, such as UV blocking and the like. In many embodiments, the attachment between the melt-processable material and the fitment and the first connector/disconnector is made without the use of adhesives, solvents or binders, which can reduce the potential for leachables and extractables in the final bag assembly.

At 560, the aseptic system and fitment combination is then connected with the bag portion. For example, the first and second walls of the bag portion can be welded or bonded to the first and second outer surfaces of the fitment and aseptic system combination such that a continuous bond or weld is formed about the entire perimeter of the bag assembly. Any suitable bonding or welding technique can be used to attach the first and second walls of the bag portion to the first and second outer surfaces of the fitment and aseptic system combination. For example, the first and second walls of the bag portion may be attached to the outer surfaces of the fitment and aseptic system combination using heat bonding, laser welding, ultrasonic welding, heat sealing, or platen welding techniques. In many embodiments, the attachment between the first and second walls of the bag portion and the first and second outer surfaces of the fitment and aseptic system combination is made without the use of adhesives, solvents or binders, which can reduce the potential for leachables and extractables in the final bag assembly. Thus, the over molded fitment and aseptic system are continuously formed, so that no leakage points exist between the bag portion and the aseptic system.

C. Continuously forming the aseptic system at the interface by welding or molding the aseptic system directly to the bag portion (at 550). In an embodiment, the aseptic system is continuously formed with the bag portion at the interface by being directed connected to the first and second walls of the bag portion so that the aseptic system is in fluid communication with the interior of the bag portion. The first and second walls of the bag portion can be welded or bonded to outer surfaces of the aseptic system such that a continuous bond or weld is formed about the entire perimeter, where any suitable bonding or welding technique discussed above for bonding or welding the fitment to the bag portion can also be used to attach the first and second walls of the bag portion to the outer surfaces of the aseptic system.

In another embodiment, the aseptic system is continuously formed with the bag portion at the interface by having a connection piece of the aseptic system connected between the first and second walls of the bag portion so that the aseptic system is in fluid communication with the interior of the bag portion. The first and second walls of the bag portion can be welded or bonded to outer surfaces of the connection piece of the aseptic system such that a continuous bond or weld is formed about the entire perimeter, where any suitable bonding or welding technique discussed above for bonding or welding the fitment to the bag portion can also be used to attach the first and second walls of the bag portion to the outer surfaces of the connection piece of the aseptic system.

Optionally, the bag portion is pressurized. Pressurizing the bag portion may be accomplished via, for example, a gas tube providing gas through the opening of the bag portion and/or through the aseptic system. Pressurizing the bag portion may be performed while the bag portion, aseptic system, and/or fitment are inside a molding cast or an ultrasonic welding device, for example by providing a gas source such as a gas tube, apertures in the cast or device, or the like. Pressurizing the bag portion expands the bag portion.

The bag assembly is then sterilized after the assembly of the bag portion, the aseptic system, and/or the fitment. For example, the bag assembly can undergo sterilization by gamma irradiation, where Cobalt 60 is used to kill microorganisms. The bag assembly can be subjected to at least 50 kGy and up to about 100 kGy, 200 kGy, 500 kGy, or 1000 kGy of gamma radiation.

After sterilization, the aseptic system is sealed so that the bag assembly remains aseptic. In an embodiment, removable films are used to seal the aseptic system to maintain the fluid passages as aseptic. It is appreciated that other devices can also be used to maintain the fluid passage as aseptic, for example, valves, caps, or similar devices.

Aspects:

It is noted that any one of aspects 1-11 can be combined with any one of aspects 12-17 or 18 or 19. Any one of aspects 12-17 can be combined with any one of aspects 1-11 or 18 or 19.

Aspect 1. A bag assembly comprising a bag portion comprising first and second walls defining an interior and an opening, wherein the interior is formed by the first and second walls of the bag portion being attached to each other along at least a portion of a perimeter of the bag assembly up to one end of the bag portion, wherein portions of the first and second walls of the bag portion that are not attached to each other form the opening, and; an aseptic system for sterile connection and disconnection of the bag assembly from a sterile process, the aseptic system being continuously formed at an interface between the aseptic system and the one end of the bag portion, wherein the aseptic system comprises an internal passage to allow fluid communication with the interior of the bag portion and the sterile process Aspect 2. The bag assembly of Aspect 1, further comprising a fitment, the fitment comprising first and second outer surfaces extending between opposing end points and a fitting extending transversely from the fitment, wherein the continuous formation at the interface is formed by the fitting of the fitment being integrally molded with the aseptic system as a single molded piece, wherein the internal passage is formed transversely through the aseptic system, the fitting, and the fitment for the fluid communication with the interior of the bag portion.

Aspect 3. The bag assembly of Aspect 2, wherein the fitment comprises a fluoropolymer, wherein the fluoropolymer of the fitment is formed of the same material as the first and second walls of the bag portion.

Aspect 4. The bag assembly of Aspect 1, further comprising a fitment, the fitment comprising first and second outer surfaces extending between opposing end points and a fitting extending transversely from the fitment, wherein the continuous formation at the interface is formed by the fitting of the fitment and the aseptic system being over molded with a melt-processable material to connect the aseptic system and the fitting of the fitment in a way such that the internal passage of the aseptic system is connected to an internal passage through the fitting and the fitment to the interior of the bag portion.

Aspect 5. The bag assembly of Aspect 1, wherein the aseptic system is continuously formed with the interface and the first and second walls of the bag portion in a way such that the internal passage is formed through the aseptic system to connect directly to the interior of the bag portion.

Aspect 6. The bag assembly of Aspect 5, wherein the interface comprises a connection piece extending transversely from the aseptic system, wherein outer surfaces of the connection piece are continuously formed with the first and second walls of the bag portion.

Aspect 7. The bag assembly of Aspect 6, wherein the connection piece has an ovular shape.

Aspect 8. The bag assembly of any one of Aspects 5-7, wherein the interface comprises a first connector/disconnector of the aseptic system, wherein the first connector/disconnector is continuously formed with the first and second walls of the bag portion.

Aspect 9. The bag assembly of any one of Aspects 1-8, wherein the bag assembly is free of adhesives, solvents, binders or combinations thereof.

Aspect 10. The bag assembly of any of Aspects 1-9, wherein each of the first and second walls comprise at least one sheet of a fluoropolymer film.

Aspect 11. The bag assembly of Aspect 10, wherein the fluoropolymer film comprises an ethylenetetrafluoroethylene polymer.

Aspect 12. A method for manufacturing a bag assembly, the method comprising the steps of: forming a bag portion of the bag assembly by attaching together first and second walls along at least a portion of a perimeter of the bag assembly up to at least one end of the bag portion to define an interior and an opening of the bag portion, wherein portions of the first and second walls of the bag portion that are not attached to each other form the opening, continuously forming an aseptic system with the one end of the bag portion by having a continuously formed interface between the aseptic system and the bag portion, the aseptic system for providing sterile connection and disconnection of the bag assembly from a sterile process, wherein the aseptic system comprises an internal passage to allow fluid communication with the interior of the bag portion and the sterile process.

Aspect 13. The method of Aspect 12, wherein the continuously formed interface is formed by integrally molding a fitting that extends transversely from a fitment with the aseptic system as a single molded piece using a single mold tool so that the internal passage is formed transversely through the aseptic system, the fitting, and the fitment to the interior of the bag portion, and the method further comprising the step of connecting the fitment with the one end of the bag portion.

Aspect 14. The method of Aspect 12, wherein the continuously formed interface is formed by over molding a melt-processable material over a connection piece of the aseptic system and a fitting that extends transversely from a fitment so that the internal passage of the aseptic system is connected to an internal passage through the fitting and the fitment to the interior of the bag portion and the method further comprising the step of connecting the fitment with the one end of the bag portion.

Aspect 15. The method of Aspect 14, wherein the connection piece of the aseptic system, the fitting of the fitment, and the melt-processable polymer material are compatible materials for molding.

Aspect 16. The method of Aspect 12, wherein the continuously formed interface is formed by welding the aseptic system with the first and second walls of the bag portion in a way such that the internal passage is formed through the aseptic system to connect directly to the interior of the bag portion.

Aspect 17. The method of any of Aspects 12-16, wherein each of the first and second walls comprise at least one sheet of a fluoropolymer film.

Aspect 18. An integrated aseptic system comprising: a fitment comprising first and second outer surfaces extending between opposing end points, the fitment comprising a fluoropolymer, an aseptic system for sterile connection and disconnection from a sterile process, the aseptic system being continuously formed with an interface between the aseptic system and the fitment, wherein the aseptic system comprises an internal passage to allow fluid communication between the fitment and the aseptic system.

Aspect 19. A bag assembly, comprising: a bag portion comprising first and second walls defining an interior and an opening, wherein the interior is formed by the first and second walls of the bag portion being attached to each other along at least a portion of a perimeter of the bag assembly up to one end of the bag portion, wherein portions of the first and second walls of the bag portion that are not attached to each other form the opening, wherein each of the first and second walls comprise at least one sheet of a fluoropolymer film, and; an aseptic system for sterile connection and disconnection of the bag assembly from a sterile process, wherein the aseptic system comprises an internal passage to allow fluid communication with the interior of the bag portion and the sterile process, with continuous formation of polymer formed at an interface between the aseptic system and the one end of the bag portion.

The terminology used in this specification is intended to describe particular embodiments and is not intended to be limiting. The terms "a," "an," and "the" include the plural forms as well, unless clearly indicated otherwise. The terms "comprises" and "comprising," when used in this specification, specify the presence of the stated features, integers, steps, operations, elements, or components, but do not preclude the presence or addition of one or more other features, integers, steps, operations, elements, or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A bag assembly comprising:
a bag portion comprising first and second walls defining an interior and an opening, wherein the interior is formed by the first and second walls of the bag portion being attached to each other along at least a portion of a perimeter of the bag assembly up to one end of the bag portion, wherein portions of the first and second walls of the bag portion that are not attached to each other form the opening,
an aseptic system for sterile connection and disconnection of the bag assembly from a sterile process, the aseptic system being continuously formed at an interface between the aseptic system and the one end of the bag portion, and;
a fitment comprising first and second outer surfaces extending between opposing end points and a fitting extending transversely from the fitment, wherein the continuous formation at the interface is formed by the fitting of the fitment and the aseptic system being over molded with a melt-processable material to connect the aseptic system and the fitting of the fitment such that the internal passage of the aseptic system is connected to an internal passage through the fitting and the fitment to the interior of the bag portion,
wherein the aseptic system comprises an internal passage to allow fluid communication with the interior of the bag portion and the sterile process.

2. The bag assembly according to claim 1, further comprising a fitment, the fitment comprising first and second outer surfaces extending between opposing end points and a fitting extending transversely from the fitment, wherein the continuous formation at the interface is formed by the fitting of the fitment being integrally molded with the aseptic system as a single molded piece, wherein the internal passage is formed transversely through the aseptic system, the fitting, and the fitment for the fluid communication with the interior of the bag portion.

3. The bag assembly according to claim 2, wherein the fitment comprises a fluoropolymer, wherein the fluoropolymer of the fitment is formed of the same material as the first and second walls of the bag portion.

4. The bag assembly according to claim 1, wherein the aseptic system is continuously formed with the interface and the first and second walls of the bag portion in a way such that the internal passage is formed through the aseptic system to connect directly to the interior of the bag portion.

5. The bag assembly according to claim 4, wherein the interface comprises a connection piece extending transversely from the aseptic system, wherein outer surfaces of the connection piece are continuously formed with the first and second walls of the bag portion.

6. The bag assembly according to claim 5, wherein the connection piece has an ovular shape.

7. The bag assembly according to claim 4, wherein the interface comprises a first connector/disconnector of the aseptic system, wherein the first connector/disconnector is continuously formed with the first and second walls of the bag portion.

8. The bag assembly according to claim 1, wherein the bag assembly is free of adhesives, solvents, and binders.

9. The bag assembly according to claim 1, wherein each of the first and second walls comprise at least one sheet of a fluoropolymer film.

10. A method for manufacturing a bag assembly, the method comprising the steps of:
forming a bag portion of the bag assembly by attaching together first and second walls along at least a portion of a perimeter of the bag assembly up to at least one end of the bag portion to define an interior and an opening of the bag portion, wherein portions of the first and second walls of the bag portion that are not attached to each other form the opening,
continuously forming an aseptic system with the one end of the bag portion by having a continuously formed interface between the aseptic system and the bag portion, the aseptic system for providing sterile connection and disconnection of the bag assembly from a sterile process,
wherein the aseptic system comprises an internal passage to allow fluid communication with the interior of the bag portion and the sterile process,
wherein the continuously formed interface is formed by over molding a melt-processable material over a connection piece of the aseptic system and a fitting that extends transversely from a fitment so that the internal passage of the aseptic system is connected to an internal passage through the fitting and the fitment to the interior of the bag portion and the method further comprising the step of connecting the fitment with the one end of the bag portion.

11. The method of claim 10, wherein the continuously formed interface is formed by integrally molding a fitting that extends transversely from a fitment with the aseptic system as a single molded piece using a single mold tool so that the internal passage is formed transversely through the aseptic system, the fitting, and the fitment to the interior of the bag portion, and the method further comprising the step of connecting the fitment with the one end of the bag portion.

12. The method of claim 10, wherein the connection piece of the aseptic system, the fitting of the fitment, and the melt-processable polymer material are compatible materials for molding.

13. The method of claim 10, wherein the continuously formed interface is formed by welding the aseptic system with the first and second walls of the bag portion in a way such that the internal passage is formed through the aseptic system to connect directly to the interior of the bag portion.

14. The method of claim 10, wherein each of the first and second walls comprise at least one sheet of a fluoropolymer film.

15. An integrated aseptic system comprising:
a fitment comprising first and second outer surfaces extending between opposing end points, the fitment comprising a fluoropolymer,
an aseptic system for sterile connection and disconnection from a sterile process, the aseptic system being continuously formed with an interface between the aseptic system and the fitment, wherein the aseptic system comprises an internal passage to allow fluid communication between the fitment and the aseptic system, and;

a fitting extending transversely from the fitment, wherein the continuous formation at the interface is formed by the fitting of the fitment and the aseptic system being over molded with a melt-processable material to connect the aseptic system and the fitting of the fitment such that the internal passage of the aseptic system is connected to an internal passage through the fitting and the fitment to an interior of a bag portion.

* * * * *